(12) United States Patent
Biel et al.

(10) Patent No.: US 11,497,250 B2
(45) Date of Patent: Nov. 15, 2022

(54) ELECTRONIC CIGARETTE WITH WOVEN FIBER TUBE ATOMIZER

(71) Applicant: Fontem Holdings 1 B.V., Amsterdam (NL)

(72) Inventors: Stefan Biel, Hamburg (DE); Vaclav Borkovec, Hamburg (DE)

(73) Assignee: Fontem Holdings 1 B.V., Amsterdam (NL)

( * ) Notice: Subject to any disclaimer, the term of this patent is extended or adjusted under 35 U.S.C. 154(b) by 8 days.

(21) Appl. No.: 16/921,650

(22) Filed: Jul. 6, 2020

(65) Prior Publication Data

US 2020/0397051 A1 Dec. 24, 2020

Related U.S. Application Data

(63) Continuation of application No. 15/565,300, filed as application No. PCT/EP2016/057777 on Apr. 8, 2016, now Pat. No. 10,701,972.

(30) Foreign Application Priority Data

Apr. 10, 2015 (EP) ..................................... 15163167

(51) Int. Cl.
*A24F 47/00* (2020.01)
*A24F 40/44* (2020.01)
*A24F 40/10* (2020.01)
*A24F 40/42* (2020.01)
*A61M 15/06* (2006.01)

(52) U.S. Cl.
CPC .............. *A24F 40/44* (2020.01); *A24F 40/10* (2020.01); *A24F 40/42* (2020.01); *A61M 15/06* (2013.01)

(58) Field of Classification Search
CPC ................................. A24F 40/44; A24F 40/46
See application file for complete search history.

(56) References Cited

U.S. PATENT DOCUMENTS

| 2011/0290269 | A1* | 12/2011 | Shimizu | A61M 11/042 131/330 |
|---|---|---|---|---|
| 2014/0000638 | A1 | 1/2014 | Sebastian et al. | |
| 2014/0224244 | A1* | 8/2014 | Liu | A24F 40/46 128/202.21 |
| 2014/0238423 | A1 | 8/2014 | Tucker et al. | |
| 2014/0238424 | A1 | 8/2014 | Marcko et al. | |
| 2014/0299141 | A1 | 10/2014 | Flick | |
| 2015/0090280 | A1 | 4/2015 | Chen | |
| 2015/0090281 | A1 | 4/2015 | Chen | |
| 2015/0245669 | A1 | 9/2015 | Cadieux et al. | |

FOREIGN PATENT DOCUMENTS

EP 2700324 A1 2/2014

\* cited by examiner

*Primary Examiner* — Eric Yaary
(74) *Attorney, Agent, or Firm* — Dykema Gossett PLLC

(57) ABSTRACT

An electronic cigarette (10) includes an atomizer (26) having a coil-less heating element (4) with a heating section (6) connected to an electrical power source and two end sections in contact with a liquid supply (34). The heating element (4) is made of one or more woven fiber tubes (2) having a hollow interior such that the liquid can be transported from the liquid supply (34) to the heating section (6) through the hollow interior along the woven fiber tubes (2) or through the fiber materials via capillary action.

14 Claims, 8 Drawing Sheets

ELECTRONIC CIGARETTE WITH WOVEN FIBER TUBE ATOMIZER

This application is a continuation of U.S. application Ser. No. 15/565,300, filed 9 Oct. 2017 (the '300 application), now issued as U.S. Pat. No. 10,701,972 issued on 7 Jul. 2020; which is the national stage application of international application no. PCT/EP2016/057777, filed on 8 Apr. 2016 (the '777 application) and published under International publication no. WO 2016/162492 on 13 Oct. 2016. This application claims priority to European patent application no. 15163167.8, filed 10 Apr. 2015 (the '167 application) and granted under European patent no. EP3078281B1 on 2 Jan. 2019. The '300 application; '777 application; and the '167 application are all hereby incorporated by reference as though fully set forth herein.

FIELD OF THE INVENTION

The field of the invention is electronic cigarettes and similar devices which use a battery powered heater to vaporize a liquid for inhalation.

BACKGROUND OF THE INVENTION

An electronic smoking device, such as an electronic cigarette (e-cigarette), typically has a housing accommodating an electric power source (e.g. a single use or rechargeable battery, electrical plug, or other power source), and an electrically operable atomizer. The atomizer vaporizes or atomizes liquid supplied from a liquid supply with a heating element and provides vaporized or atomized liquid as an aerosol. Control electronics control the activation of the atomizer. In some electronic cigarettes, an airflow sensor is provided within the electronic smoking device which detects a user puffing on the device (e.g., by sensing an underpressure or an air flow pattern through the device). The airflow sensor indicates or signals the puff to the control electronics to power up the device and generate vapor. In other e-cigarettes, a switch is used to power up the e-cigarette to generate a puff of vapor.

The heating element of conventional atomizers uses metallic heating wires wrapped around porous wick materials (such as cotton or silica). Alternatively, coil-less heating elements can be used in improved atomizers. Both designs require an element to transport liquid to the heating section of the heating element. Engineering challenges accordingly remain in providing improved atomizers for electronic cigarettes.

SUMMARY OF THE INVENTION

In accordance with one aspect of the present invention there is provided an electronic smoking device including a housing, one or more woven fiber tubes in the housing, and a liquid supply in the housing. At least one of the woven fiber tubes has an electrically conductive heating section and one or more end sections. A first side of the heating section is connected to a first lead, and a second side of the heating section is connected to a second lead. Both the first and the second leads are connectable to an electrical power source. One or more end sections of the woven fiber tube are in contact with the liquid supply.

In some embodiments, the entire woven fiber tube is electrically conductive. The woven fiber tube may be made of different materials to provide desirable properties such as electrical conductivity, liquid conductivity, strength, etc. The woven fiber tube has a hollow interior such that the liquid can be transported through the hollow interior via capillary action. Additionally, the liquid can be transported through the porous material of the fiber wall of the tube. The woven fiber tube can form any shape, for example, U-shape, C-shape or L-shape, with one or more ends in contact with the liquid in the liquid supply. The woven fiber tubes can have the same diameter or different diameters. Moreover, the heating section of the woven fiber tube can have a different diameter from the end sections of the woven fiber tube. When multiple woven fiber tubes are used, they can be positioned essentially parallel to each other and/or in direct contact with each other. A liquid supply of any configuration can be used to provide continuous liquid flow to the heating section. For example, the liquid supply may contain free-flowing liquid or comprise a porous medium that stores liquid. One or more ends of the woven fiber tubes are in contact with the liquid supply to transport the liquid to the heating section.

The characteristics, features and advantages of this invention and the manner in which they are obtained as described above, will become more apparent and be more clearly understood in connection with the following description of exemplary embodiments, which are explained with reference to the accompanying drawings.

BRIEF DESCRIPTION OF THE DRAWINGS

In the drawings, the same element number indicates the same element, in each of the views.

FIG. 6 is a schematic illustration of an alternative design of the liquid supply, which forms a prismatic shape having a cross-section of a circle with a segment missing to allow for airflow if positioned within a cylindrical sleeve. Either end or both ends of the heating element 4 can be inserted into the liquid supply 34. The gap 52 created between the liquid supply 34 and the sleeve 50 allows air to flow through.

DETAILED DESCRIPTION

Figure 1:
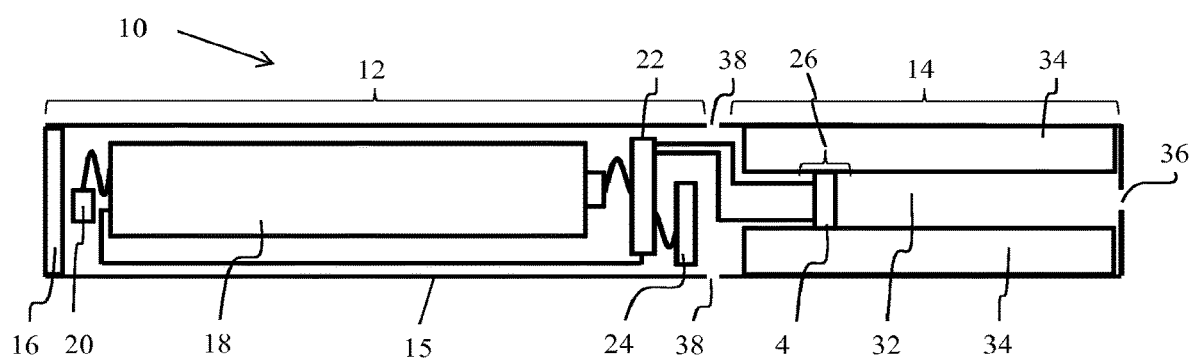
FIG. 1 is a schematic illustration of an electronic cigarette or similar vaporizing device.

As is shown in FIG. 1, an e-cigarette 10 typically has a housing comprising a cylindrical hollow tube having an end cap 16. The cylindrical hollow tube may be a single piece or a multiple piece tube. In FIG. 1, the cylindrical hollow tube is shown as a two piece structure having a battery portion 12 and an atomizer/liquid supply portion 14. Together the battery portion 12 and the atomizer/liquid supply portion 14 form a cylindrical tube which is approximately the same size and shape as a conventional cigarette, typically about 100 mm with a 7.5 mm diameter, although lengths may range from 70 to 150 or 180 mm, and diameters from 5 to 20 mm.

The battery portion 12 and atomizer/liquid supply portion 14 are typically made of steel or hardwearing plastic and act together with the end caps to provide a housing to contain the components of the e-cigarette 10. The battery portion 12 and the atomizer/liquid supply portion 14 may be configured to fit together by a friction push fit, a snap fit, or a bayonet attachment, magnetic fit, or screw threads. The end cap 16 is provided at the front end of the battery portion 12. The end cap 16 may be made from translucent plastic or other translucent material to allow an LED 20 positioned near the end cap to emit light through the end cap. The end cap can be made of metal or other materials that do not allow light to pass.

An air inlet may be provided in the end cap, at the edge of the inlet next to the cylindrical hollow tube, anywhere along the length of the cylindrical hollow tube, or at the connection of the battery portion 12 and the atomizer/liquid supply portion 14. FIG. 1 shows a pair of air inlets 38 provided at the intersection between the battery portion 12 and the atomizer/liquid supply portion 14.

A battery 18, a light emitting diode (LED) 20, control electronics 22 and optionally an airflow sensor 24 are provided within the cylindrical hollow tube battery portion 12. The battery 18 is electrically connected to the control electronics 22, which is electrically connected to the LED 20 and the airflow sensor 24. In this example the LED 20 is at the front end of the battery portion 12, adjacent to the end cap 16, and the control electronics 22 and airflow sensor 24 are provided in the central cavity at the other end of the battery 18 adjacent the atomizer/liquid supply portion 14.

The airflow sensor 24 acts as a puff detector, detecting a user puffing or sucking on the mouthpiece in the atomizer/liquid supply portion 14 of the e-cigarette 10. The airflow sensor 24 can be any suitable sensor for detecting changes in airflow or air pressure such a microphone switch including a deformable membrane which is caused to move by variations in air pressure. Alternatively the sensor may be a Hall element or an electro-mechanical sensor.

The control electronics 22 are also connected to an atomizer 26. In the example shown, the atomizer 26 includes a heating element 4 which is extending across a central passage 32 of the atomizer/liquid supply portion 14. The heating element 4 does not completely block the central passage 32. Rather, an air gap is provided on either side of the heating element 4 enabling air to flow past the heating element 4. The atomizer may alternatively use other forms of heating elements, such as ceramic heaters, or fiber or mesh material heaters. Nonresistance heating elements such as sonic, piezo and jet spray may also be used in the atomizer in place of the heating coil.

The central passage 32 is surrounded by a cylindrical liquid supply 34 with one or both ends of the heating element 4 extending into the liquid supply 34. In other embodiments the liquid supply 34 may comprise a toroidal cavity arranged to be filled with liquid and with one or both ends of the heating element 4 extending into the toroidal cavity.

Figure 6:
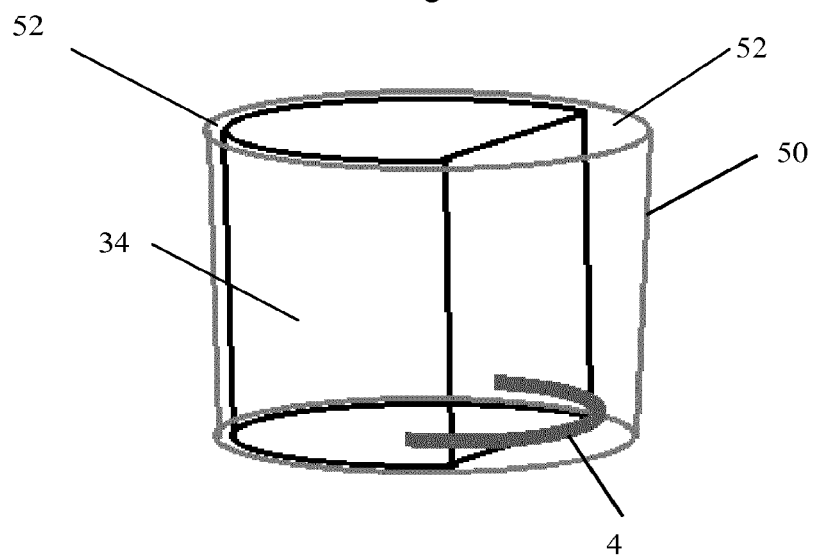

Alternatively, the liquid supply 34 can be a prismatic reservoir that has a cross-section of a circle with a segment missing to allow for airflow if positioned within a cylindrical sleeve as shown in FIG. 6.

The liquid supply may contain free-flowing liquid. Alternatively, the liquid supply may be made from a porous medium in which the liquid is stored.

An air inhalation port 36 is provided at the back end of the atomizer/liquid supply portion 14 remote from the end cap 16. The inhalation port 36 may be formed from the cylindrical hollow tube atomizer/liquid supply portion 14 or may be formed in an end cap.

In use, a user sucks on the e-cigarette 10. This causes air to be drawn into the e-cigarette 10 via one or more air inlets, such as air inlets 38 and to be drawn through the central passage 32 towards the air inhalation port 36. The change in air pressure which arises is detected by the airflow sensor 24 which generates an electrical signal that is passed to the control electronics 22. In response to the signal, the control electronics 22 activates the heating element 4 which causes liquid present in the heating element to be vaporized creating an aerosol (which may comprise gaseous and liquid components) within the central passage 32. As the user continues to suck on the e-cigarette 10, this aerosol is drawn through the central passage 32 and inhaled by the user. At the same time the control electronics 22 also activates the LED 20 causing the LED 20 to light up which is visible via the translucent end cap 16 mimicking the appearance of a glowing ember at the end of a conventional cigarette. As liquid present in the heating element 4 is converted into an aerosol, more liquid is drawn into the heating element 4 from the liquid supply 34 by capillary action and thus is available to be converted into an aerosol.

Some e-cigarettes are intended to be disposable and the electric power in the battery 18 is intended to be sufficient to vaporize the liquid contained within the liquid supply 34 after which the e-cigarette 10 is thrown away. In other embodiments the battery 18 is rechargeable and the liquid supply is refillable. In the cases where the liquid supply 34 is a toroidal cavity, this may be achieved by refilling the liquid supply via a refill port. In other embodiments the atomizer/liquid supply portion 14 of the e-cigarette 10 is detachable from the battery portion 12 and a new atomizer/liquid supply portion 14 can be fitted with a new liquid supply 34, thereby replenishing the supply of liquid. In some cases, replacing the liquid supply 34 may involve replacement of the heating element 4 along with the replacement of the liquid supply 34.

The new liquid supply 34 may be in the form of a cartridge having a central passage 32 through which a user inhales aerosol. In other embodiments, aerosol may flow around the exterior of the cartridge 32 to an air inhalation port 36.

In addition to the above description of the structure and function of a typical e-cigarette 10, variations also exist. For example, the LED 20 may be omitted. The airflow sensor 24 may be placed adjacent to the end cap 16 rather than in the middle of the e-cigarette. The airflow sensor 24 may be replaced with a switch which enables a user to activate the e-cigarette manually rather than in response to the detection of a change in air flow or air pressure.

In one aspect, a coil-less atomizer need not have a separate wicking element to deliver liquid to the heating section. The coil-less atomizer has a C-, L- or U-shaped heating element made of one or more woven fiber tubes having a hollow interior. One or both ends of the heating element are in contact with the liquid in a liquid supply such that the woven fiber tube can deliver the liquid to the heating section due to its capillary action.

The woven fiber tube can be made of carbon fibers, nickel-chromium, steel, titanium, iron-chromium-aluminum, molybdenum disilicide, silicon carbide, silicon dioxide, Dacron, ceramic fibers, or any combination thereof. The woven fiber can be, for example, woven carbon fiber. The woven fiber tube also can be made from a composite woven fibrous material. The composite can be manufactured from fibers from two different materials: one for electrical resistance heating, and one for capillary liquid flow: e.g. nickel-chromium woven with silicon dioxide. One of these materials can also include high temperature resistant polymers such as Dacron for added strength. Other examples can include carbon fiber woven with Dacron, or ceramic fibers such as alumina mixed with stainless steel.

The conductive properties and the capillary properties of the woven fiber tube allow replacement of two components of a conventional electronic cigarette, the heating wire and the porous wick materials, with a single component, the woven fiber tube. The reduced size of the atomizer may allow more space in the electronic cigarettes. Thus, the coil-less atomizers disclosed can be miniaturized electronic cigarettes for other components relative to conventional coil atomizers for electronic cigarettes, to provide more compact designs for electronic cigarettes.

A section of the woven fiber tube may be coated with a conductive material to reduce the electrical resistance of the fibers. The conductive fiber material may be shaped to have areas of lesser and greater resistance.

In another aspect, an electronic cigarette includes a coil-less atomizer having a heating element with a first lead, a second lead, and one or more woven fiber tubes electrically connected to the first and second leads. Alternatively, the heating element does not need any lead to conduct electricity. Rather, electricity can be conducted by a first electrical contact and a second electrical contact located on the surface of the woven fiber tube(s). A mid-section of the woven fiber tube between the leads or the electrical contacts forms a heating section.

The woven fiber tube may further comprise a first and a second conductive sections. The first and the second conductive sections are proximal to the first and second leads or electrical contacts, respectively. The first and second conductive sections may have low electrical resistances (e.g., about 1Ω or less) relative to the electrical resistance of the heating section which has a higher electrical resistance (e.g., about 3Ω to about 5Ω, or about 1Ω to about 7Ω). The heating element may be designed to have a desired total electrical resistance of about 3Ω to about 6Ω, or about 1Ω to about 8Ω. For example, the total electrical resistance is between 0.5 and 5.0Ω, between 1 and 4Ω or between 1.5 and 3.8Ω. When the e-cigarette is switched on, electricity flows between the electrodes through the conductive sections and the heating section. Electric current flowing through the heating element generates heat at the heating section, due to the higher resistance of the heating section.

A sheet of woven fiber having a predefined area can be bent and rolled into a tube having a hollow interior by connecting the opposite edges of the woven carbon fiber sheet. The weave pattern affects the electrical resistance per cm$^3$ of material. It is within the purview of one of ordinary skill in the art to determine the weave pattern, thickness of the material, the positions of the connecting portions to obtain desired electrical resistance.

The weave orientation of the different materials depends on what properties they are being used for. For example, when a sheet of carbon fiber woven with Dacron is used, the Dacron is used for added strength. Therefore, the woven fiber sheet is rolled into a tube in the axis of likely bending. In another example, when carbon fiber is woven with silicon dioxide fiber bundles, the silicon dioxide fiber is used for enhanced wicking. Therefore, then woven fiber sheet is rolled into a tube in the direction of desired liquid flow.

Figure 2:
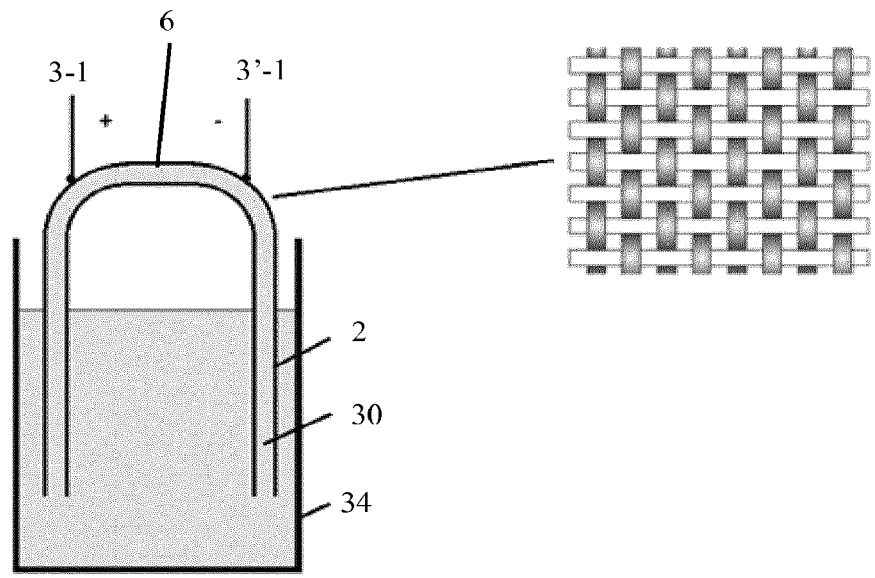
FIG. 2 is a schematic illustration of a piece of woven carbon fiber sheet rolled into a U-shape tube with both ends of the tube immersed in the liquid of a liquid supply and with a heating section formed between two electrical contacts.

FIG. 2 shows a piece of woven carbon fiber sheet, which is rolled into a U-shaped woven carbon fiber tube 2 with both ends immersed in the liquid of a liquid supply 34. Electrical contacts 3-1 and 3'-1 are placed on the U-shaped woven carbon fiber tube to form a heating section 6 between the electrical contacts.

In this example, woven carbon fiber tube 2 extends beyond the electrical contacts and bends into a U-shape such that both ends of the tube are immersed in liquid supply 34. The liquid is transported inside the hollow interior along the woven carbon fiber tube(s) to heating element 4 via capillary action.

Alternatively, leads 3 and 3' can be used as electrodes on the woven carbon fiber tube(s) such that electricity is conducted through leads onto the heating element.

Figure 3:
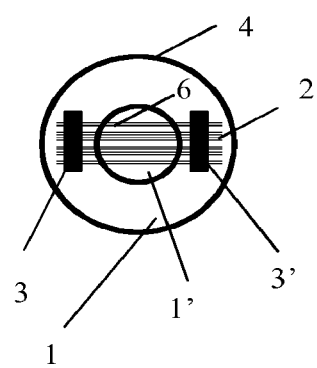
FIG. 3 is a top view of a coil-less heating element having two leads on woven fiber tube(s).

FIG. 3 shows a heating element 4 with the woven fiber tubes 2 of the heating element mounted on a board 1 between two leads 3 and 3'. The board maybe a printed circuit board (PCB) with other electrical components, or it may be a board where the only electrical component is the heating element 4. The board may be an insulating material that provides sufficient support for the heating element, for example fiberglass. The woven fiber tubes between the two leads 3 and 3' form the heating section 6. The board 1 may have a through hole 1' at least partially overlapping with part of the heating section 6 (e.g. overlapping with about 30% to about 100%, about 50% to about 100%, about 90% to about 100%, or about 100% of the heating section). The leads 3 and 3' may be made of any conductive materials. The woven fiber tubes 2 extend laterally beyond the leads 3 and 3' to be in contact with the liquid in a liquid supply such that the liquid can be transferred along or through the tube(s) to the heating section. If more than one woven fiber tube 2 is used, the tubes may be positioned substantially parallel to each other between the leads 3 and 3', wherein the largest angle between a woven carbon fiber tube and a line connecting the leads 3 and 3' is about 0 to about 10°, about 0 to about 5°, or about 0 to about 2°.

The liquid supply can be in any configuration as long as the liquid supply provides continuous liquid flow through the U-shaped heating element. For example, if the thickness of the fiber material is very thick and the diameter of the hollow interior of the fiber tube is very small then most of the wicking is conducted via the porosity of the fiber material (permitting liquid transfer from a porous medium). Accordingly, the liquid supply may be made from a porous medium containing the liquid. Conversely, if the fibre material is very thin and the fiber tube has a relatively large diameter then most of the wicking is conducted via the capillary action through the hollow interior of the fiber tube. Accordingly, the liquid supply may contain free-flowing liquid to provide a continuous flow to the heating section. In some embodiments, the liquid supply contains both free-flowing liquid and liquid stored in porous medium.

The conductive material used to make leads 3 and 3' may be porous electrode materials, including, conductive ceramics (e.g. conductive porous ceramics and conductive foamed ceramics), foamed metals (e.g. Au, Pt, Ag, Pd, Ni, Ti, Pb, Ba, W, Re, Os, Cu, Ir, Pt, Mo, Mu, W, Zn, Nb, Ta, Ru, Zr, Pd, Fe, Co, V, Rh, Cr, Li, Na, Tl, Sr, Mn, and any alloys thereof), porous conductive carbon materials (e.g. graphite, graphene and/or nanoporous carbon-based materials), stainless steel fiber felt, and any composites thereof. Conductive ceramics may comprise one or more components selected from the group consisting of oxides (e.g. $ZrO_2$, $TrO_2$, $SiO_2$, $Al_3O_2$, etc.), carbides (e.g. SiC, $B_4C$), nitrides (e.g. AlN), any of the metals listed above, carbon (e.g. graphite, graphene, and carbon-based materials), Si, and any combinations and/or composites of these materials. The term "composite" of two or more components means a material obtained from at least one processing of the two or more components, e.g. by sintering and/or depositing.

Figure 4:
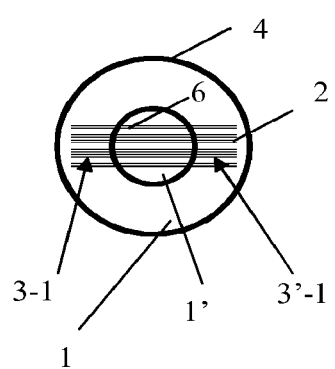
FIG. 4 is a top view of a coil-less heating element having two electrical contacts on the woven fiber tube(s).

Alternatively, leads are not needed for the heating element with a woven carbon fiber tube due to electrical conductivity of the carbon fiber material. FIG. 4 shows that at the predefined locations of the woven carbon fiber tubes, two electrical contacts can be made. The locations of the electrical contacts can be the same as or different from the locations of the leads.

For clarity of illustration, FIG. 3 and FIG. 4 schematically show the woven fiber tubes in the heating element. One or more woven fiber tubes can be used and the tubes can be arranged parallel to each other and/or in contact with each other. This configuration allows two mechanisms for transporting the liquid: the liquid is transported from the hollow interior of the fiber tube via capillary action and the liquid is transported by direct contact of the porous fiber material. Either or both mechanisms contribute to liquid transportation in the exemplified electronic cigarettes.

The diameter of the hollow interior of the woven carbon fiber tube is between 0.1 mm and 3 mm, preferably between 0.5 mm and 2 mm such that the liquid is drawn from a liquid supply and delivered to the heating section through the hollow interior via capillary action.

It is within the purview of one of ordinary skill in the art to optimize the diameter of the tube to deliver the liquid to the heating section. The distance or height h that the liquid travels by capillary action can be calculated by the following formula:

$$h = \frac{2\gamma \cos\theta}{\rho g r},$$

where γ is the liquid-air surface tension (force/unit length), θ is the contact angle, ρ is the density of the liquid (mass/volume), g is local acceleration due to gravity (length/square of time), and r is radius of the tube. Accordingly, the smaller the radius or diameter of the tube, the further the liquid travels.

When the liquid is transported through the porous fiber material, the capillary forces can be calculated by Darcy's equation:

$$q = \frac{-\kappa}{\mu} \nabla p,$$

where q is the flux (discharge per unit area, with units of length per time, m/s) and ∇p is the pressure gradient vector (Pa/m).

The weighting of the terms of both equations to collaboratively describe the fluid flow depends on the ratio of wall porosity (thickness of the carbon fiber material) to capillary tube diameter (inner diameter of the fiber tube).

In some embodiments, multiple woven fiber tubes are used and arranged adjacent to each other such that a sufficient amount of liquid is drawn to the heating section and vaporized. For example, the woven fiber tubes can be essentially parallel to each other. The woven fiber tubes also can be in direct contact with each other to facilitate the transport of liquid from one tube to another tube in direct contact.

When multiple woven fiber tubes are used, the tubes may have the same diameter or different diameters. For example, one tube having the largest diameter can be in the center while tubes of smaller diameters can be arranged on both sides of the tube having the largest diameter. In one embodiment, only the tube having the largest diameter has a heating section while the surrounding tubes of smaller diameters do not have a heating section and function as supply tubes to transport liquid to the heating section of the center tube having a heating section.

Figure 7:
FIG. 7 illustrates an exemplary configuration of the arrangement of woven fiber tubes.

FIG. 7 illustrates a woven fiber tube having a large diameter in direct contact with woven fiber tubes having a small diameter. The smaller woven fiber tubes primarily provide extra wicking from a liquid supply via capillary flow through the hollow interior. The large woven fiber tube has a defined heating section and draws liquid from the adjacent smaller woven fiber tubes via its porous wall.

Additionally, multiple woven fiber tubes having various diameters may be combined to achieve a staged delivery of aerosol. For example, if a woven fiber tube having a small diameter is positioned next to a woven fiber tube having a large diameter, and both tubes contain heating sections, then the smaller tube has a lower thermal mass than the larger tube, thus heating up faster. This will provide a staged delivery of aerosol when power is applied to improve flavor experience.

Figure 8:
FIG. 8 illustrates an alternative configuration of woven fiber tubes having various diameters.

FIG. 8 illustrates an alternative configuration of woven fiber tubes having various diameters. When woven fiber tubes having various diameters are arranged in direct contact with each other, it provides two separate fluid flow directions: one along the axis of each tube through the hollow interior, and the other direction perpendicular to the axis of each tube through direct contact of the porous material. Accordingly, this configuration provides improved liquid flow.

In some embodiments, different sections of a single woven carbon fiber tube may have different diameters. For example, the heating section is positioned in the center of the tube and has the largest diameter while the sections adjacent to the heating section have a smaller diameter such that the heating section has a "bubble" configuration. The liquid is transported through the sections having a smaller diameter adjacent to the heating section. Once the liquid reaches the "bubble" shaped heating section, the capillary transport will stop such that the amount of the liquid is sufficient to form an inside coating in the bubble section rather than accumulating too much liquid in the bubble section. Thus, a sufficient amount of the liquid will be vaporized without overfilling the heating section. This reduces the thermal inertia of the larger heating tube allowing a faster aerosol production time from the moment that the power is applied. In this configuration, additional supply tubes having smaller diameters can be used and arranged in contact with the tube having the "bubble" section.

The woven carbon fiber sheet can have different weave patterns, such as 2/2 twill, plain weave, satin weave, harness weave, fish weave, etc. The weave pattern affects the stiffness and strength of the element. Splined fiber arrangements are usually quite soft and delicate whereas woven fibers are usually more robust and can be packed in a higher density. The resistance of the fiber depends on the cross sectional area of the element that it is made from: lots of small fibers or some large fibers will produce the same resistance. Small fibers are better for wicking to a certain extent, whereas larger fibers may be stronger but more brittle.

The woven carbon fiber sheet or the woven carbon fiber tube may be modified to improve surface properties (e.g. better hydrophilic properties to enhance wicking abilities) by exposure/coating/adhering the fiber sheet or the fiber tube to compounds having hydrophilic groups (e.g. hydroxide groups).

Moreover, a woven material comprised of a breathable membrane material, e.g. a micro porous membrane from expanded polytetrafluoroethylene (ePTFE) such as Gortex, or a fiber material having a desirable pore size can be used to allow gas, air or vapor exchange.

The woven fiber sheet or the woven fiber tube may also be modified to have desired electrical or thermal properties. For example the electrical or thermal conductivity of the fiber material may be changed by applying one or more modifying materials onto the fiber material. In general, metal-coated fibers have increased electrical and thermal conductivity in comparison to the non-coated fibers. The modifying material may be applied to the fiber material by coating, adhering, sputtering, plating, or otherwise depositing the modifying material onto the fiber material.

In e-cigarette operation using the heating element shown in FIG. 3 or FIG. 4, liquid from a liquid supply is provided to the heating section through the woven fiber tube(s). As the user inhales on the e-cigarette, vaporized liquid mixes with air flowing through the hole 1' which at least partially overlaps with part of heating section 6 (e.g. overlapping with about 30% to about 100%, about 50% to about 100%, about 90% to about 100%, or about 100% of the heating section).

Figure 5:
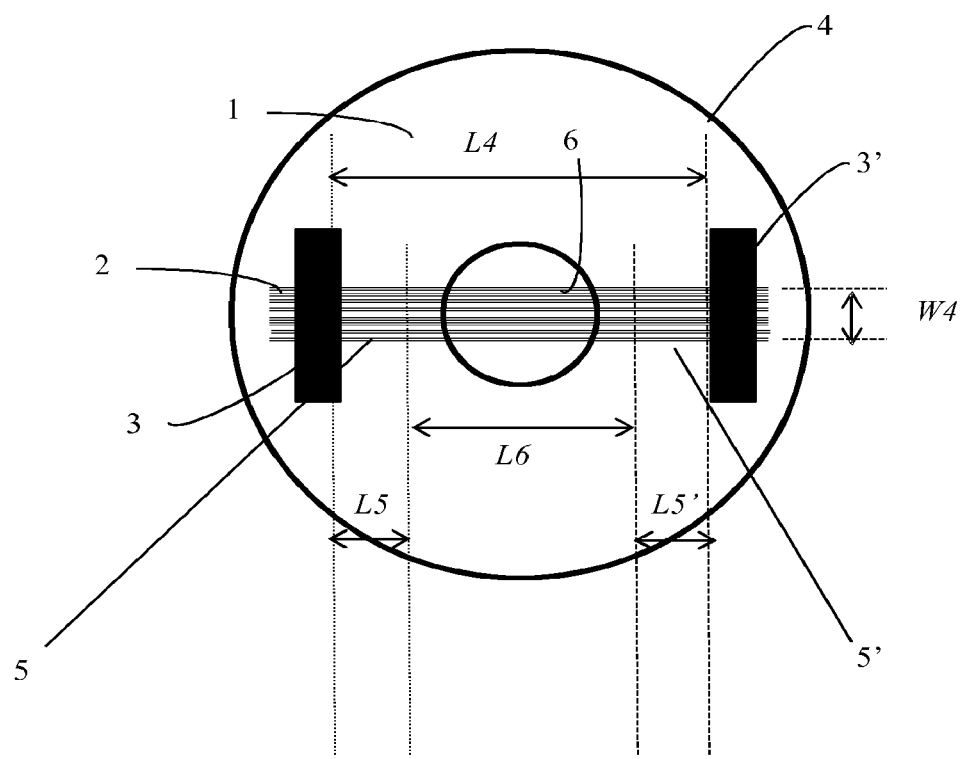
FIG. 5 is a top view of a coil-less heating element having coated woven fiber tube(s).

FIG. 5 illustrates another heating element 4 where the woven carbon fiber tube(s) 2 are mounted on a board 1 between two leads 3 and 3' or two electrical contacts 3-1 and 3'-1. The woven carbon fiber tube(s) extend laterally beyond the leads or the electrical contacts to be in contact with the liquid in a liquid supplying unit. The woven carbon fiber tube(s) between the leads or electrical contacts have a first conductive section 5 electrically connected to a first lead 3 or a first electrical contact 3-1, a second conductive section 5' electrically connected to a second lead 3' or a second electrical contact 3'-1, and a heating section 6 between first conductive section 5 and second conductive section 5'. Conductive sections 5 and 5' have lower electrical resistance relative to heating section 6. Heating section 6 and leads or electrical contacts may have electrical resistances selected so that the total electrical resistance of heating element 4 is suitable for the operation of an electric cigarette typically operating with DC battery voltage of from about 3 to 5 volts. In this case heating element 4 may have a resistance of about 3~5Ω, or about 3.8Ω at room temperature.

Electrical resistance of a conductor can be calculated by the following formula:

$$R = \rho \frac{l}{A},$$

where R is electrical resistance (Ω), l is the length of the conductor, A is the cross-sectional area of the conductor (m²), and ρ is the electrical resistivity of the material (Ω m).

The areas of the woven carbon fiber tube(s) in relation to the current may not be significantly different between conductive sections 5 and 5' (A5, A5') and heating section 6 (A6). However, the electrical resistance of the conductive sections should be lower than the heating section. This may be achieved by selectively modifying different sections of the woven carbon fiber tube(s), as described above, to reduce the resistance of the conductive sections, and/or to increase the resistance of the heating section.

Figure 9A:
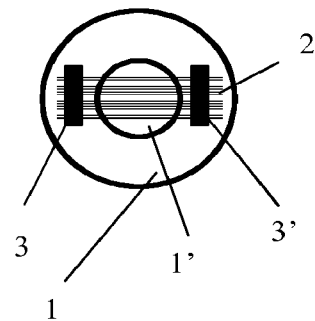
FIGS. 9A-9D illustrate a method of coating conductive fibers to make the coil-less heating element shown in FIG. 3.
Figure 9B:
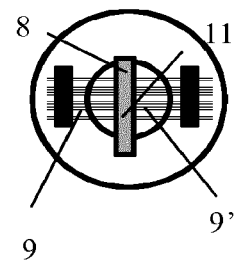
Figure 9C:
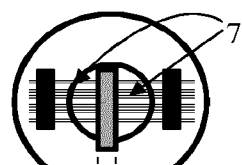
Figure 9D:
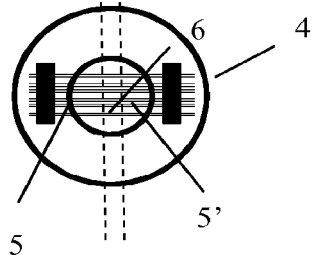

FIGS. 9A-9D show a manufacturing process of the coil-less heating element shown in FIG. 3, which may include the following steps:

a) installing one or more woven fiber tubes 2 on a board 1 between a first lead 3 and a second lead 3' (FIG. 9A). The board 1 has a through hole 1' between the first and second leads 3 and 3'.

b) covering a portion of the fibers between the first lead 3 and the second lead 3' with a mask 8 to provide a masked portion of the woven fiber tube(s) 11 and unmasked portions of the woven fiber tube(s) 9 and 9' (FIG. 9B). The through hole 1' at least partially overlaps with part of the masked portion of the woven fiber tube(s) 11.

c) sputtering or otherwise applying at least part of the unmasked portions of the woven fiber tube(s) 9 and 9' with a modifying agent 7 as described above, with the modifying agent 7 having a lower electrical resistance than the woven fiber tube(s) before sputtering (FIG. 9C).

d) removing the mask 8 to provide a heating element as illustrated in FIG. 3 (FIG. 9D).

The coil-less heating element shown in FIG. 4 can be manufactured by a similar process except that step a) entails installing one or more woven fiber tubes on a board between two predefined locations for electrical contacts to be made.

Figure 10:
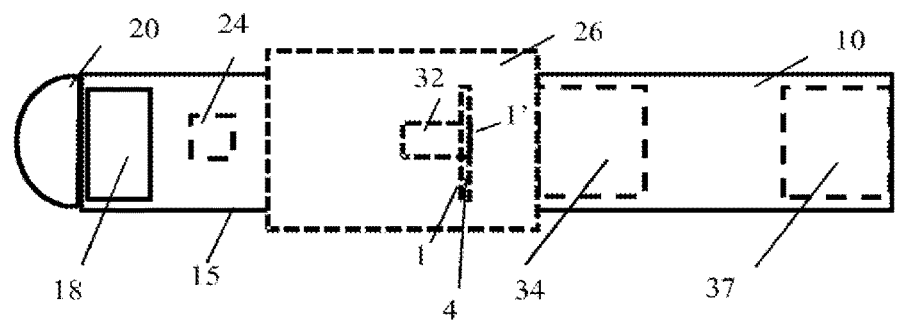
FIG. 10 shows an electronic cigarette having a coil-less atomizer, a liquid supply, a power source, a mouth piece, an LED, and a sensor.

FIG. 10 shows an electronic cigarette 10 having a coil-less atomizer 26 and a liquid supply 34. The coil-less atomizer 26 includes a coil-less heating element 4 as illustrated in FIG. 3, 4, or 5, and an airflow central passage 32 through at least part of the atomizer. The heating element 4 has a board 1 having a through hole T. The electronic cigarette 10 may further include an electrical power source 18, such as a battery or an electrical connector to a power source, a mouth piece 37, one or more LEDs 20 which light up in operation, and a sensor 24 within a housing 15.

The coil-less atomizer 26 is also wickless. A separate wicking element is not needed because the woven carbon fiber tube(s) allows a liquid to flow directly from liquid tank 34 to coil-less heating element 4 via capillary action.

Figure 11:
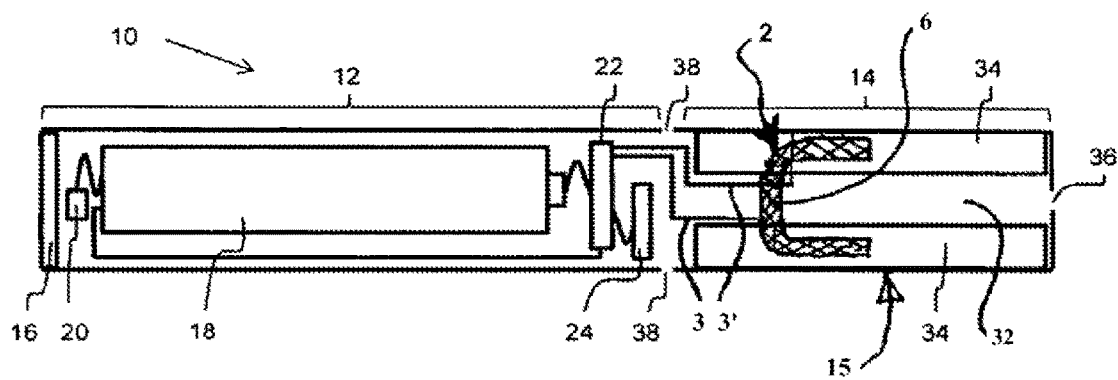
FIG. 11 shows an electronic cigarette having the coil-less heating element of FIG. 3, 4 or 5.

FIG. 11 illustrates an exemplary e-cigarette having the U-shaped heating element described above. In the example shown, the atomizer 26 includes a woven fiber tube 2, for example made of carbon fibers. One or both ends of the fiber tube 2 project into the liquid supply 34. The fiber tube 2 may be positioned anywhere in the atomizer. Although shown as a U-shape, the tube may have other shapes as well, such as C-shaped or L-shaped, with the mid-section 32 of the fiber tube 2 oriented perpendicularly or in parallel to the axis of the housing 15.

Wire leads 3 and 3' or electrical contacts 3-1 and 3'-1 from the control electronics 22 are connected to opposite sides of the heating section 6. The fibers forming the tube 2 are electrically conductive. The fibers also conduct liquid via capillary action. Consequently, the fiber tube 2 acts as both a heating element and a wicking element. In use, when the control electronics 22 provides electric current via the leads 3 and 3' to the fiber tube 2, the heating section 6 of the tube heats up. Liquid on or inside of the heating section 6 of the fiber tube 2 is vaporized. Additional liquid from the liquid supply 34 moves via capillary action on or through the ends of the fiber tube 2 to the heating section 6, replacing the vaporized liquid.

In an alternative design, only the heating section 6 of the fiber tube 2 is electrically conductive, while the ends are not, so that the ends of the fiber tube 2 only conduct liquid but not electric current. Generally, the fiber tube 2 is hollow. However, it may be modified by filling in the inside of the fiber tube 2 with porous media such as wadding or fiber bundles to store the liquid.

Figure 12:
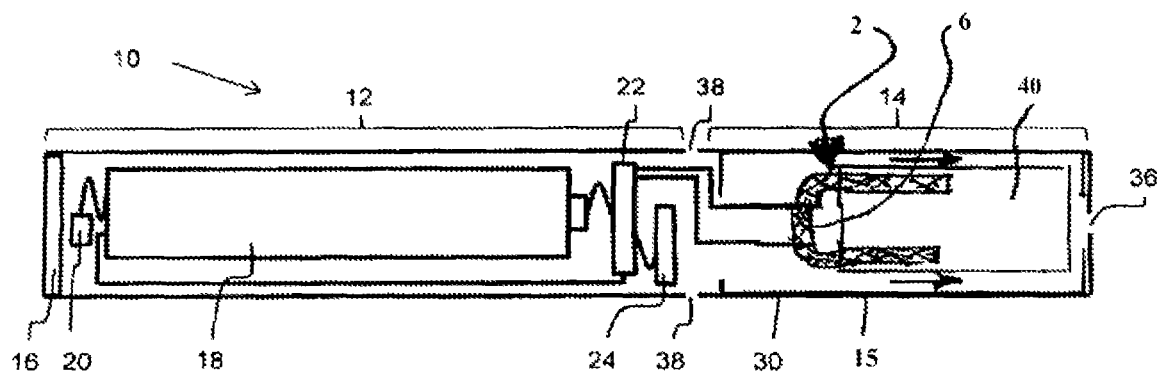
FIG. 12 shows an alternative design of an electronic cigarette having the coil-less heating element of FIG. 3, 4 or 5.

FIG. 12 shows a design where a bottle or other container 40 holds the liquid. In this design, the ends of the fiber tube 2 may extend into the container 40 through a gland or compression fitting, which allows liquid to move out of the bottle through the fiber tube 2 by capillary action, while preventing leaking of bulk liquid into the housing 15.

In the design of FIG. 12, the operation is similar, but with the vapor flowing out through an annular space, or discrete slots, between the container 40 and the inner walls of the housing 15.

The heating elements described can be efficiently and conveniently produced in mass production, at low cost. They can also be manufactured with precise control of electrical resistance, leading to better performance when used in an electronic cigarette. The heating elements described may also be made in small sizes providing greater versatility for use in electronic cigarettes.

The coil-less atomizer described above may alternatively be described as an electrically conductive liquid wick having a heating section. The heating section may be defined by an area of the wick having higher electrical resistance than other sections of the wick, so that electrical current passing through the wick heats the heating section to a high temperature, such as 100 to 350° C., while other sections of the wick and the ends of the wick which are in contact with a bulk liquid source, remain relatively unheated. The wick, as a single element, heats liquid to generate vapor at the heating section, and also conveys liquid from the bulk liquid source to the heating location. The electrically conductive liquid wick is made of woven carbon fiber that can conduct electrical current, heat and liquid through the wick material, and with the electrical resistance of the wick non-uniform to provide a distinct heating section. The heating section can be treated to create different electrical resistances between the heating section and other sections. Generally the wick has a single heating section in the center or close to the center and two ends immersed into a liquid supplying unit.

The heating section of the wick may be oriented perpendicular to air flow within an electronic cigarette, with air flowing around the wick, rather than through the wick. Within the atomizing chamber or space, the wick may be perpendicular to the air flow and not loop back on itself, and also not extend longitudinally or parallel to the direction of air flow. In an electronic cigarette having dimensions comparable to a conventional tobacco cigarette (5-10 or 12 mm in diameter and 80-120 mm long), the bulk liquid source contains enough liquid for at least 100 puffs and up to 500 puffs (typically 0.1 to 2 mL).

Prophetic Example 1. A Coil-Less Atomizer as Shown in FIG. 3, Prepared According to the Process Illustrated in FIGS. 9A-9D One or more woven carbon fiber tubes 2 are installed to a circular PCB 1 between two metal leads 3 and 3' or between two predefined locations where electrical contacts 3-1 and 3'-1 are to be made. The board has a through hole 1' between the two leads 3 and 3' or the two electrical contacts 3-1 and 3'-1. A mask 8 is placed to cover a portion (about 3 to about 4 mm lateral) of the woven carbon fiber tubes between the leads 3 and 3' or the electrical contacts 3-1 and 3'-1 to provide a masked portion of the woven carbon fiber tube 11 and unmasked portions of the woven carbon fiber tube 9 and 9'. The through hole 1' overlaps with the masked portion of the woven carbon fiber tube 11. The unmasked portions of the woven carbon fiber tube 9 and 9' are sputtered with Cr. The mask 8 is removed to provide a heating element 4 as illustrated in FIG. 3.

As used herein, "about" when used in front of a number means±10% of that number. Reference to fibers includes fiber material (woven or non-woven). Reference to liquid here means liquids used in electronic cigarettes, generally a solution of propylene glycol, vegetable glycerin, and/or polyethylene glycol 400 mixed with concentrated flavors and/or nicotine, and equivalents. Each of the elements in any of the embodiments described may of course also be used in combination with any other embodiment. Reference to electronic cigarettes includes electronic cigars and pipes, as well as components of them, such as cartomizers.

The examples and embodiments described herein are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein.

The invention claimed is:

1. An electronic smoking device comprising:
    a housing;
    an electrically conductive wick comprising
        a first conductive section including a first wick end,
        a heating section, and
        a second conductive section including a second wick end, where the heating section, between the first conductive section and the second conductive section, has a higher electrical resistance than the first and the second conductive sections; and
        wherein the electrically conductive wick is a bent woven sheet connected on opposite edges of the sheet; and
    a liquid source, wherein the first wick end and the second wick end are in fluid contact with the liquid source.

2. The device of claim 1, wherein the electrically conductive wick comprises carbon fibers, nickel-chromium, steel, titanium, iron-chromium-aluminum, molybdenum disilicide, silicon carbide, silicon dioxide, Dacron, ceramic fibers, or a combination thereof.

3. The device of claim 2, wherein the electrically conductive wick includes a plurality of fibers, wherein the fibers are woven in a weave pattern comprising one or more of a 2/2 twill weave, a plain weave, a satin weave, a harness weave, and a fish weave.

4. The device of claim 1, further comprising a printed circuit board, wherein the electrically conductive wick is coupled with the printed circuit board.

5. The device of claim 1, wherein the heating section is substantially perpendicular to a longitudinal axis of the housing.

6. The device of claim 1, wherein the heating section comprises:
    a first side connected to a first electrical contact or a first lead; and a second side connected to a second electrical contact or a second lead;

wherein the first or the second electrical contacts or the first and second leads are connectable to an electrical power source; and one or more of the first conductive section and the second conductive section are in contact with the liquid supply.

7. The device of claim 1, wherein the electrically conductive wick is U-shaped, L-shaped, or C-shaped.

8. The device of claim 1, wherein the heating section is straight and the first and second conductive sections are longer than the heating section.

9. The device of claim 1, wherein the first and second conductive sections are perpendicular to the heating section of the electrically conductive wick.

10. The device of claim 1, wherein the device comprises two or more electrically conductive wicks.

11. The device of claim 10, wherein the two or more electrically conductive wicks are positioned in parallel to each other.

12. The device of claim 10, wherein the two or more electrically conductive wicks are positioned in direct contact of each other.

13. The device of claim 1, wherein the liquid supply contains free-flowing liquid.

14. The device of claim 1, wherein the liquid supply comprises a porous medium that stores liquid.

* * * * *